United States Patent
Hu et al.

(10) Patent No.: US 10,441,373 B2
(45) Date of Patent: Oct. 15, 2019

(54) MASTER-SLAVE SAME-STRUCTURE TELEOPERATION FRACTURE REDUCTION MECHANISM

(71) Applicants: BEIHANG UNIVERSITY, Beijing (CN); THE GENERAL HOSPITAL OF THE PEOPLE'S LIBERATION ARMY, Beijing (CN)

(72) Inventors: Lei Hu, Beijing (CN); Peifu Tang, Beijing (CN); Tianmiao Wang, Beijing (CN); Lihai Zhang, Beijing (CN); Changsheng Li, Beijing (CN); Hailong Du, Beijing (CN); Lifeng Wang, Beijing (CN); Yiming Tan, Beijing (CN); Lu Zhao, Beijing (CN)

(73) Assignees: BEIHANG UNIVERSITY, Beijing (CN); THE GENERAL HOSPITAL OF THE PEOPLE'S LIBERATION ARMY, Beijing (CN)

( * ) Notice: Subject to any disclaimer, the term of this patent is extended or adjusted under 35 U.S.C. 154(b) by 527 days.

(21) Appl. No.: 15/310,781

(22) PCT Filed: Sep. 19, 2014

(86) PCT No.: PCT/CN2014/000856
§ 371 (c)(1),
(2) Date: Nov. 13, 2016

(87) PCT Pub. No.: WO2015/172271
PCT Pub. Date: Nov. 19, 2015

(65) Prior Publication Data
US 2017/0079732 A1 Mar. 23, 2017

(30) Foreign Application Priority Data
May 12, 2014 (CN) .......................... 2014 1 0198120

(51) Int. Cl.
*A61B 34/35* (2016.01)
*A61B 17/88* (2006.01)
(Continued)

(52) U.S. Cl.
CPC .......... *A61B 34/35* (2016.02); *A61B 17/8866* (2013.01); *A61B 34/37* (2016.02);
(Continued)

(58) Field of Classification Search
CPC ...... A61B 34/35; A61B 34/37; A61B 17/8866
See application file for complete search history.

(56) References Cited

U.S. PATENT DOCUMENTS

| 2014/0107569 A1* | 4/2014 | Fischer | A61M 5/3287 604/95.01 |
| 2014/0296637 A1* | 10/2014 | Lee | A61B 1/00133 600/118 |
| 2014/0364870 A1* | 12/2014 | Alvarez | A61F 9/008 606/130 |

* cited by examiner

Primary Examiner — Andrew Yang

(57) ABSTRACT

A master-slave same structure teleoperation fracture reduction mechanism includes a frame assembly, two parallel platform assemblies, a top platform connecting plate (9), an operating handle assembly, two fixing assemblies, a controller (15), six movement assemblies and 24 hydraulic pipes (26). The operating handle assembly is located in the middle of the upper platform (5), and the two fixing assemblies are located on the top of the parallel platform assembly. The two parallel platform assemblies are disposed on the frame assembly; the controller (15) and the six movement assemblies are disposed on the frame assembly; A top platform connecting plate (9) is connected to the fixing assembly parallel platform assembly. The hydraulic pipes (26) is in communication with motion hydraulic cylinders (7a) and the other end of the hydraulic pipes is in commu- (Continued)

nication with one of platform hydraulic cylinders (7*b*). The invention assists a doctor to achieve fracture reduction.

1 Claim, 5 Drawing Sheets

(51) Int. Cl.
*A61B 34/37* (2016.01)
*A61B 34/30* (2016.01)
*A61B 17/00* (2006.01)
*A61B 17/56* (2006.01)

(52) U.S. Cl.
CPC ............... *A61B 2017/00539* (2013.01); *A61B 2017/564* (2013.01); *A61B 2034/304* (2016.02)

MASTER-SLAVE SAME-STRUCTURE TELEOPERATION FRACTURE REDUCTION MECHANISM

CROSS REFERENCE OF RELATED APPLICATION

This is a U.S. National Stage under 35 U.S.C 371 of the International Application PCT/CN2014/000856, filed Sep. 19, 2014, which claims priority under 35 U.S.C. 119(a-d) to CN 201410198120.7, filed May 12, 2014;

BACKGROUND OF THE PRESENT INVENTION

Field of Invention

The present invention relates to a master-slave same-structure teleoperation fracture reduction mechanism, belonging to surgical device field.

Description of Related Arts

The conventional method is open reduction which depends on a doctor's experiment. Open reduction turns a simple fracture into a compound fracture due to surgery. The incision is exposed in the air which may destroy the blood supply and leads to bone necrosis that delays or prevents the healing. The long operation time and high work intensity make it hard to guarantee the result of the reduction. The intramedullary nail technology is able to deal the above-mentioned problem while during the operation the doctor needs to continuously X-Ray the patient and both the doctor and patient receive high-dose radiation. Precise reduction is hard to realize due to the information captured during the operation is 2-D. Besides, after the surgery the bone may rotate and cause malreduction. The emergency of fracture reduction system solves the problems such as the femoral shaft fracture reduction system published in "*Design of a parallel long bone fracture reduction robot with planning treatment tool*" by Gramham A. E. from the university of Auckland and some Chinese patents for example "*fracture reduction device*" (CN 20081005456.3). But the result of the conventional research in this respect is not intelligent enough and manipulability is low.

Master-slave teleoperation mechanism is able to give the operator a very real sense of the interaction between the terminal of the mechanism and the operated object and the environment, which is widely applied in the industrial control, aerospace, military, remote surgery etc. The conventional researches include "*Development of a hydraulic parallel link type of force display improvement of manipulability using disturbance observer and its application to a master-slave system*" by Shigeki Kudomi and other researchers, "*Position controller based on state observer for 6-DOF parallel teleoperation manipulator*" by Gong Mingde and so forth. The result of the conventional researches has low precision and is not practical for real-time operation.

SUMMARY OF THE PRESENT INVENTION

In order to overcome the problems in conventional technology, an object of the present invention is to provide a master-slave same-structure teleoperation fracture reduction mechanism to assist the doctor to carry out fracture reduction operation.

Accordingly, in order to accomplish the above objects, the present invention comprises a frame assembly, two parallel platform assemblies, a top platform connecting plate (9), an operating handle assembly, two fixing assemblies, a controller (15), six movement assemblies and 24 hydraulic pipes (26) wherein the operating handle assembly is located in the middle of an upper platform of an operation handle parallel platform assembly; two fixing assemblies are located on the top of a fixing assembly parallel platform assembly; the two parallel platform assemblies are disposed on a top plane of the frame assembly; the controller (15) and the six movement assemblies are disposed on a middle plane of the frame assembly; a top platform connecting plate is fixedly connected to the upper platform of the fixing assembly parallel platform assembly; the hydraulic pipes is in communication with motion hydraulic cylinders (7a) in the movement assembly and platform hydraulic cylinders (7b) in the parallel platform assemblies.

The frame assembly comprises a bottom support frame (1), a U-shape frame (2), support frame connecting plate (3) and 4 universal wheels (4), wherein the bottom support frame (1) and U-shape frame (2) are connected by standard bolt; U-shape frame (2) and support frame connecting plate (3) are connected by standard bolt; bottom support frame (1) and 4 universal wheels are connected by standard bolts respectively; the support frame (1) is a cubical frame structure assembled by several rod structures, which is for supporting a main body of the present invention and placing components; the U-shape frame (2) is a U-shape structure which is for connecting the bottom support frame (1) and the support frame connecting plate (3); the support frame connecting plate (3) is a rectangle plate which is for connecting the fixing assemblies; the universal wheels (4) are standard castors which are for supporting and moving the present invention;

The parallel platform assemblies comprises the upper platform (5), twelve universal joints (6), six platform hydraulic cylinders (7b) and a lower platform (8), wherein the upper platform (5) and the lower platform (8) are fixedly connected with one proximal end of each of the universal joints; two ends of the platform hydraulic cylinder (7b) is fixedly connected with a proximal end of each of the universal joints respectively; the upper platform (5) is a round plate and the lower platform (8) is a ring-shaped plate which is for supporting each of the parallel platforms; the universal joints (6) is standard universal joints which are for connecting platform hydraulic cylinder (7b), the upper platform (5) and the lower platform (8); the platform hydraulic cylinder (7b) is a standard hydraulic cylinder which is for support components of each of the parallel platform;

A bottom end of the top platform connecting plate (9) is fixedly connected with the upper platform (5) of the fixing assembly parallel platform and an upper end of the top platform connecting plate (9) is fixedly connected with one of the fixing assemblies, wherein the top platform connecting plate (9) is a plate with a boss which is for connecting one of the parallel platform assemblies and one of the fixing assemblies;

The operating handle assemblies comprises an operating handle (10) and an operating button (11), wherein the operating handle (10) is connected with the upper platform (5) of the operation handle parallel platform and the operating button (11) is fixedly connected with the operating handle (10); the operating handle (10) is a column with a round plate on one end which is for handheld operating the parallel platform assembly, wherein the operating button (11) is a standard button which is for on/off control the controller (15);

Each of the fixing assemblies comprises a fixing baseplate (12), two baseplate connecting blocks (13) and two curved poles (14), wherein the fixing baseplate (12) is connected with support frame connecting plate (3) and the top platform connecting plate (9) respectively; the baseplate connecting blocks (13) are embedded in a groove on the fixing baseplate (12) and fixedly connected with the fixing baseplate (12) by standard bolts; the curved poles (14) are fixedly connected with the baseplate connecting blocks (13), wherein the fixing baseplate (12) is a plate with one groove on each of the two sides which is for fixing the baseplate connecting block (13); the baseplate connecting blocks (13) is a cubic structure with threaded holes which is for connecting the fixing baseplate (12) and the curved poles (14), wherein each of the curved poles (14) is a pole structure with a curve on one end which is for connecting a fixing nail fixed on broken bones;

the controller (15) is fixedly connected with the bottom support frame (1), wherein the controller (15) is a standard controller which is for collecting signals from encoders (18), limit switches (19) and hydraulic sensors (25) and controlling the motion of DC motors (17);

Each of the movement assembly comprises a fixing platform (16), a DC motor (17), a encoder (18), two limit switches (19), a guide rail (20), a sliding block (21), a screw rod (22), a sliding block connector (23), two motion hydraulic cylinders (7a), a hydraulic cylinder connector (24), four hydraulic sensors (25), wherein the fixing platform (16) is fixedly connected with the bottom support frame (1); the guide rail (20) is fixedly connected with the fixing platform; two limit switches (19) are assembled on two ends of the fixing platform (16); the screw rod (22) is connected with two ends of the fixing platform (16); the sliding block (21) is connected with the screw rod (22) and the guide rail (20), wherein the sliding block connector (23) is fixedly connected with the sliding block (21) and a piston rod of the motion hydraulic cylinders (7a); the hydraulic cylinder connector (24) is fixedly connected with the motion hydraulic cylinders (7a) and fixing platform (16); a bottom end of each of the hydraulic sensors (25) is fixedly connected with the motion hydraulic cylinder (7a) and a upper end of each of the hydraulic sensors (25) is fixedly connected with the platform hydraulic cylinder (7b) through one of the hydraulic pipes (26); the DC motor (17) is fixedly connected with the fixing platform (16) and the screw rod (22); the encoder (18) is fixedly connected with the DC motor (17); the fixing platform (16) is a U-shaped structure with two mounting holes which is for fixing the movement assembly and components; wherein the DC motor (17) is a standard DC motor which is for driving the screw rod (22); the encoder (18) is a standard encoder which is for collecting velocity and acceleration information of the DC motor (17); the limit switches (19) are standard limit switches which is for checking the position of the sliding block; the guiding rail (20) is a standard guiding rail which guides the sliding block (21), wherein the sliding block (21) is a threaded cubic sliding block which is for transforming a rotary motion of the screw rod (22) into a translational motion; the screw rod (22) is a standard screw rod which is for connecting the DC motor (17) and sliding block (21); the sliding block connector (23) is an L-shaped structure with two through holes which is for connecting the sliding block (21) and the two motion hydraulic cylinders (7a); the hydraulic cylinder connector (24) is an L-shaped structure with two through holes which is for connecting the fixing platform (16) and the two motion hydraulic cylinder (7a); the hydraulic sensors (25) are standard which is for checking liquid pressure in the hydraulic pipes (26)

Twelve of the 24 hydraulic pipes (26) is connected with the movement assemblies and the operating handle parallel platform assemblies and the rest twelve hydraulic pipes are connected with the movement assemblies and the fixing assembly parallel platform assemblies which are connected with the top platform connecting plate (9) and the fixing assemblies, wherein the hydraulic pipes are standard hydraulic pipes for power transfer for parallel platform and movement assemblies.

Compared with the conventional technology, the present invention has the following benefits:

1. the present mechanism reduces the work intensity of the doctor by adopting force scaling control strategy and frees the doctor from manual reduction;
2. the parallel platform adopts 6-DOF (degrees of freedom) parallel mechanism which is high precision, high workload, high rigidity, and is able to be operated in reasonable working space with a compact structure.
3. the present invention enables the doctor to operate on the patient out of the surgical site, which reduces the X-Ray radiation received by the doctor.
4. the present invention adopts a master-slave structure which enhances the ease of operation by connecting the operation end and slave end by hydraulic pipes to make the pose of the slave end is exactly same with the operation end.

Element reference: 1—bottom support frame, 2—U—shape frame, 3—support frame connecting plate, 4—universal wheel, 5—upper platform, 6—universal joint, 7a—motion hydraulic cylinder, 7b—platform hydraulic cylinder, 8—lower platform, 9—top platform connecting plate, 10—operating handle, 11—operating button, 12—fixing baseplate, 13—baseplate connecting block, 14—curved pole, 15—controller, 16—fixing platform, 17—DC motor, 18—encoder, 19—limit switch, 20—guide rail, 21—sliding block, 22—screw rod, 23—sliding block connector, 24—hydraulic cylinder connector, 25—hydraulic sensor, 26—hydraulic pipe.

DETAILED DESCRIPTION OF THE PREFERRED EMBODIMENT

Figure 1:
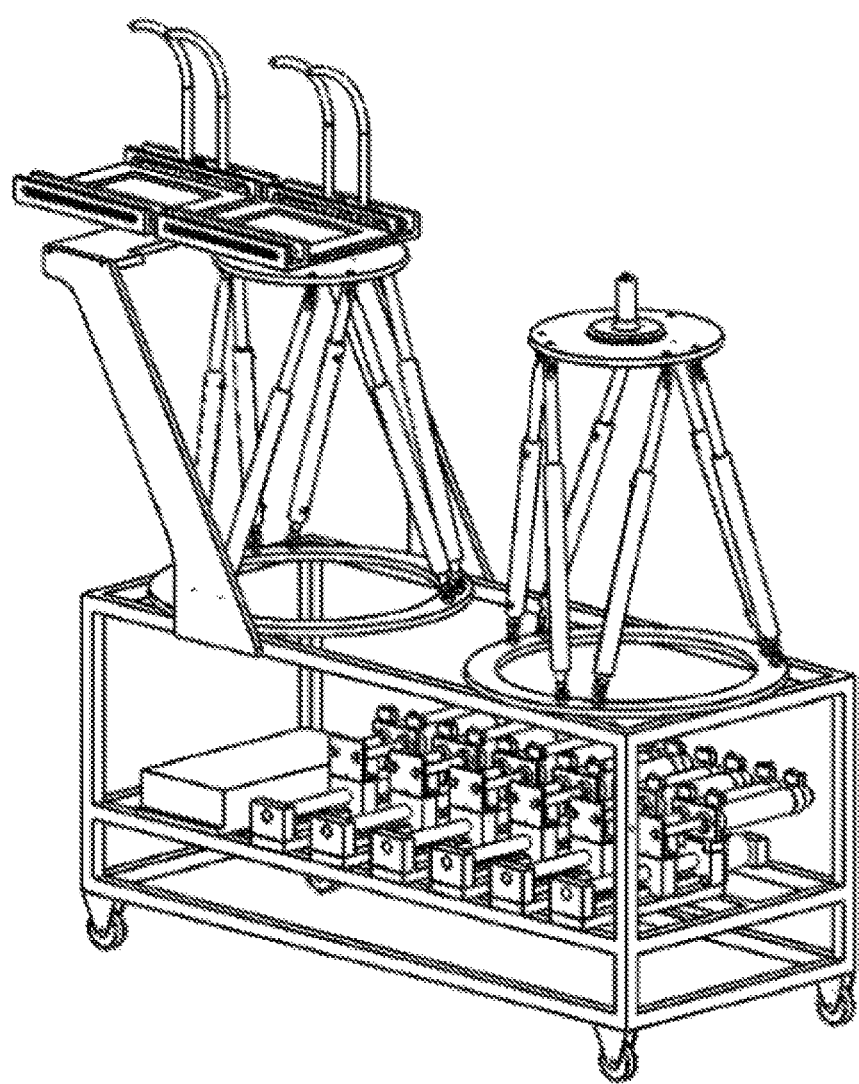
FIG. 1 is a perspective view of a master-slave same-structure teleoperation fracture reduction mechanism.
Figure 2:
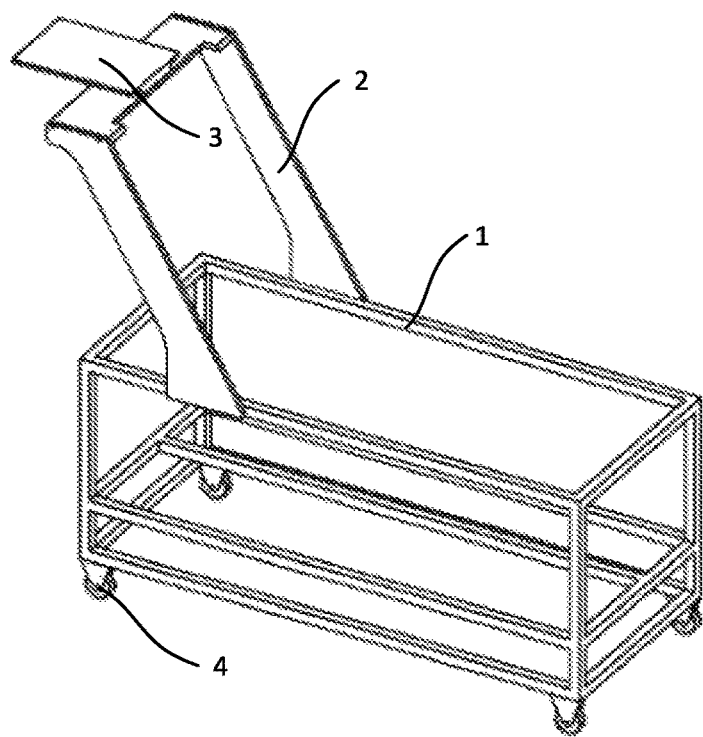
FIG. 2 is a perspective view of a frame assembly.
Figure 3:
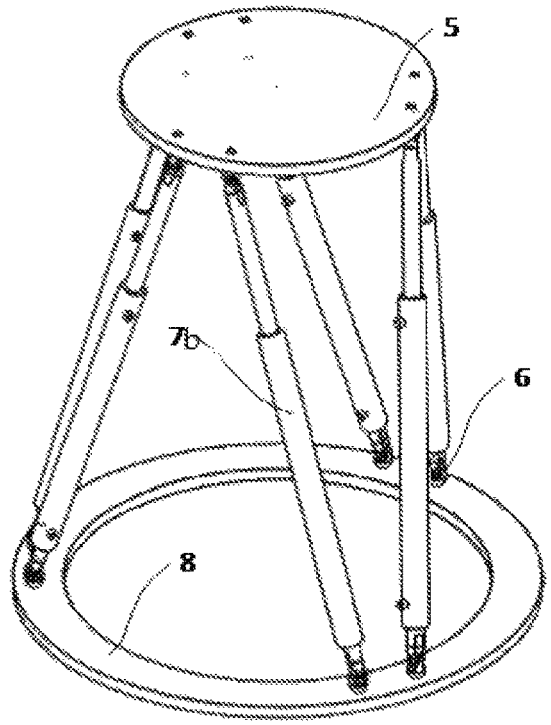
FIG. 3 is a perspective view of a parallel platform assembly.
Figure 4:
FIG. 4 is a perspective view of a top platform connecting plate.
Figure 5:
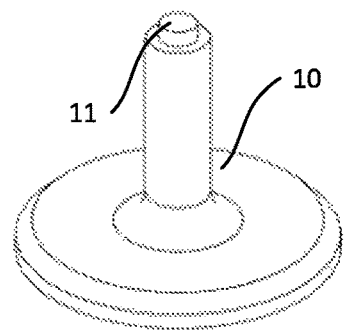
FIG. 5 is a perspective view of an operating handle assembly.
Figure 6:
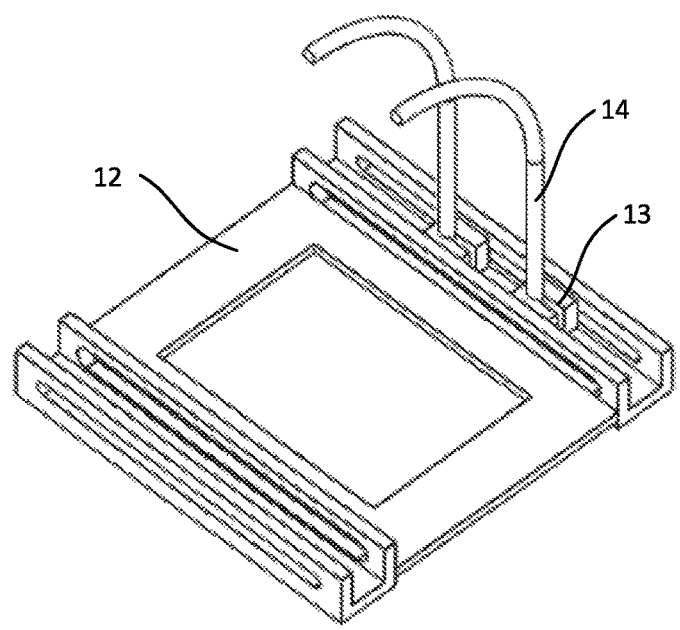
FIG. 6 is a perspective view of a fixing assembly.
Figure 7:
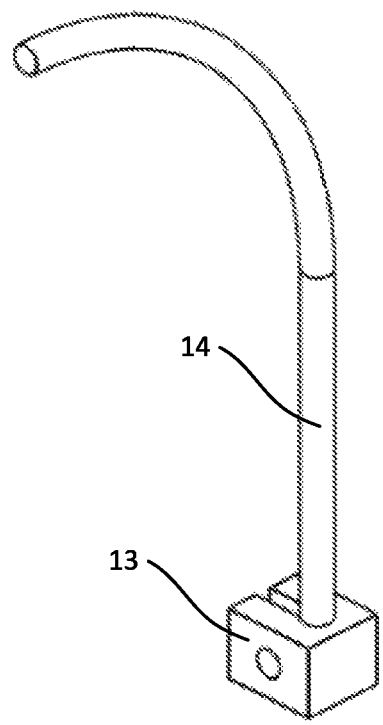
FIG. 7 is a perspective view of a baseplate connecting block and a curved pole.
Figure 8:
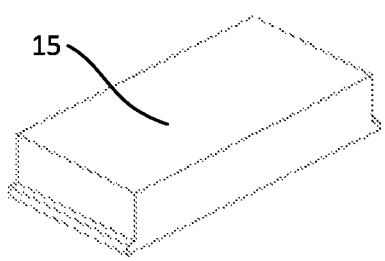
FIG. 8 is a controller.
Figure 9:
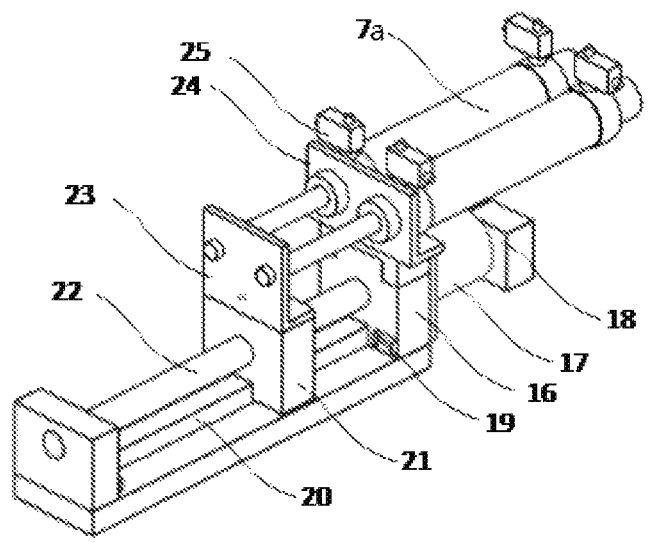
FIG. 9 is a perspective view of a movement assembly.
Figure 10:
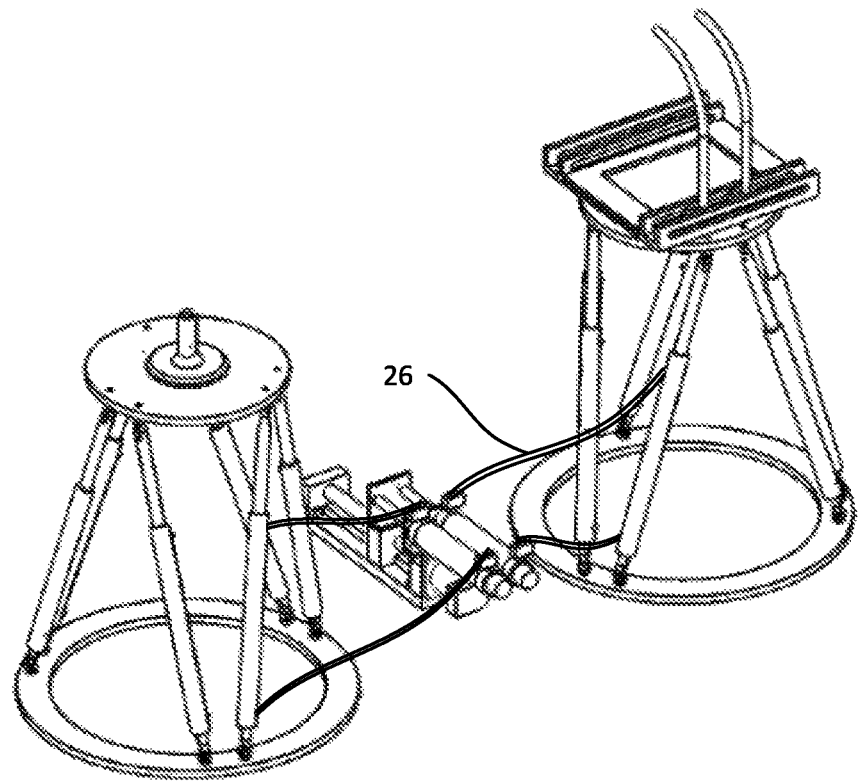
FIG. 10 illustrates the connection of hydraulic cylinder in one movement assembly.

Referring to FIG. 1 to FIG. 10 of the drawings, according to a preferred embodiment of the present invention is illustrated, wherein A master-slave same-structure teleoperation fracture reduction mechanism comprises a frame assembly, two parallel platform assemblies, a top platform connecting plate 9, an operating handle assembly, two fixing assemblies, a controller 15, six movement assemblies and 24 hydraulic pipes 26. The universal wheel 4 is able to walk in straight line and turn. Each of the parallel platform assemblies has 6-DOF. The operating handle parallel platform acts as operation end and fixed connected with the operating handle assembly. The fixing assembly parallel assembly acts as the slave end which connected with the top platform connecting plate 9 and one of the fixing assembly. Each of the universal joints 6 has 2-DOF. The piston rod of the hydraulic cylinders 7a and 7b are able to move along the cylinder's axis. The first of the two fixing assemblies is connected with the U-shape frame 2 by the support frame connecting plate 3. The second of the two fixing assemblies is fixed connected with the parallel platform which acts as the slave end by the top platform connecting plate 9. The position of the baseplate connecting block 13 is able to be adjusted in the groove on the fixing baseplate before fixed by common bolts. Driven by the DC motor 17 the screw rod 22 is able to rotate and push the sliding block 21 moves along the guide rail. The sliding block touches the limit switches 19 on the limit position at two ends of the fixing platform and drives the piston rod reciprocating in the motion hydraulic cylinder 7a through the sliding block connector 23. Each of the movement assemblies comprises two motion hydraulic cylinders 7a, the rod end and oil outlet of the first cylinder 7a is connected with the rod end and oil outlet of each of the cylinder 7b in the operating handle parallel assembly which acts as the operation end by one of the hydraulic sensor 25 and one hydraulic pipe 26 respectively. The rod end and oil outlet of the second cylinder 7a are connected with the rod end and oil outlet of each of the cylinder 7b in the fixing assembly parallel assembly which acts as the slave end by one of the hydraulic sensor 25 and one hydraulic pipe 26 respectively. The hydraulic cylinder 7b on the operating handle parallel assembly, the two hydraulic cylinder 7a on the movement assembly and the piston rod of the hydraulic cylinder 7a on the fixing assembly parallel assembly are able to move back and forth synchronously.

The present invention work in the following procedure: plant two fixing nail in the two ends of the broken bone and adjust the position of baseplate connecting block 13 in the groove on the fixing baseplate 12 to connect the fixing nails with the curved poles; turn on the operating handle 11 and control the movement of the operating handle parallel assembly by the operating handle 10; Check the oil pressure in the hydraulic pipe 26 by the hydraulic sensor 25, which is pressure of the hydraulic cylinder 7b in the operating handle parallel assembly; Feedback the pressure to the controller 15 in which works out the force taken by the piston rod; After scale-up the calculated force acts as the given signal for the position increment of the hydraulic cylinder 7b in the fixing assembly parallel assembly which acts as the slave end; In the meantime feedback the position and velocity signal of the DC motor 17 checked by encoder 18 to the controller 15; Calculates the given signal and feedback signal with closed-loop control strategy before send the signal to the DC motor 17 to control the movement of the piston rod in the hydraulic cylinder 7b in the fixing assembly parallel assembly. The pose of the fixing assembly parallel assembly is thus controlled and fulfill the fracture reduction operation.

One skilled in the art will understand that the embodiment of the present invention as shown in the drawings and described above is exemplary only and not intended to be limiting. It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A master-slave same-structure teleoperation fracture reduction mechanism, comprising: a frame assembly, two parallel platform assemblies with similar structure of six-degree-of-freedom, a top platform connecting plate (9), an operating handle assembly, two fixing assemblies for connecting broken bones, a controller (15), six movement assemblies and 24 hydraulic pipes (26); wherein the operating handle assembly is located in a middle of an upper platform (5) of an operation handle parallel platform assembly; two fixing assemblies are located on a top of a fixing assembly parallel platform assembly; the two parallel platform assemblies are disposed on a top plane of the frame assembly; the controller (15) and the six movement assemblies are disposed on a middle plane of the frame assembly; the top platform connecting plate (9) is fixedly connected to the fixing assembly parallel platform assembly; a first end of each of the hydraulic pipes (26) is in communication with one of motion hydraulic cylinders (7a) in the movement assembly and a second end of each of the hydraulic pipes is in communication with one of platform hydraulic cylinders (7b);

wherein the frame assembly comprises a bottom support frame (1), a U-shape frame (2), a support frame connecting plate (3) and 4 universal wheels (4), wherein the bottom support frame (1) and the U-shape frame (2) are connected by a standard bolt; the U-shape frame (2) and the support frame connecting plate (3) are connected by a standard bolt; the bottom support frame (1) and the 4 universal wheels are connected by standard bolts respectively; the support frame (1) is a cubical frame structure assembled by several rod structures, which is for supporting a main body of the master-slave same-structure teleoperation fracture reduction mechanism and placing components; the U-shape frame (2) is a U-shape structure which is for connecting the bottom support frame (1) and the support frame connecting plate (3); the support frame connecting plate (3) is a rectangle plate which is for connecting the fixing assemblies; the universal wheels (4) are standard castors which are for supporting and moving the master-slave same-structure teleoperation fracture reduction mechanism;

wherein each of the parallel platform assemblies comprises the upper platform (5), twelve universal joints (6), six platform hydraulic cylinders (7b) and a lower platform (8), wherein the upper platform (5) and the lower platform (8) are fixedly connected with a first end of each of the universal joints; both ends of the platform hydraulic cylinders (7b) are fixedly connected with a second end of each of the universal joints respectively; the upper platform (5) is a round plate and the lower platform (8) is a ring-shaped plate which is for supporting each of the parallel platforms; the universal joints (6) are standard universal joints which are for connecting platform hydraulic cylinders (7b), the upper platform (5) and the lower platform (8); each of the platform hydraulic cylinders (7b) is a standard hydraulic cylinder which is for support components of each of the parallel platform;

wherein a bottom end of the top platform connecting plate (9) is fixedly connected with the upper platform (5) of the fixing assembly parallel platform and a top end of the top platform connecting plate (9) is fixedly connected with one of the fixing assemblies, wherein the top platform connecting plate (9) is a plate with a boss, which is for connecting one of the parallel platform assemblies and one of the fixing assemblies;

wherein the operating handle assembly comprises an operating handle (10) and an operating button (11), wherein the operating handle (10) is connected with the upper platform (5) of the operating handle parallel platform assembly and the operating button (11) is fixedly connected with the operating handle (10); the operating handle (10) is a column with a round plate on one end, which is for manually operating the parallel platform assemblies, wherein the operating button (11) is a standard button which is for on/off control the controller (15);

wherein each of the fixing assemblies comprises a fixing baseplate (12), two baseplate connecting blocks (13) and two curved poles (14), wherein the fixing baseplate (12) is connected with the support frame connecting plate (3) and the top platform connecting plate (9) respectively; the baseplate connecting blocks (13) are embedded in grooves on the fixing baseplate (12) and fixedly connected with the fixing baseplate (12) with standard bolts; the curved poles (14) are fixedly connected with the baseplate connecting blocks, wherein the fixing baseplate (12) is a plate with the grooves on both sides, which is for fixing the baseplate connecting blocks (13); the baseplate connecting blocks (13) is a cubic structure with threaded holes which is for connecting the fixing baseplate (12) and the curved poles (14), wherein each of the curved poles (14) is a pole structure with a curve on one end, which is for connecting a fixing nail fixed on broken bones;

wherein the controller (15) is fixedly connected with the bottom support frame (1), wherein the controller (15) is a standard controller which is for sampling signals from encoders (18), limit switches (19) and hydraulic sensors (25); and controlling the motion of a DC (direct current) motors (17);

wherein each of the movement assembly comprising a fixing platform (16), the DC motor (17), one of the encoders (18), two limit switches (19), a guide rail (20), a sliding block (21), a screw rod (22), a sliding block connector (23), two motion hydraulic cylinders (7a), a hydraulic cylinder connector (24), four hydraulic sensors (25), wherein the fixing platform (16) is fixedly connected with the bottom support frame (1); the guide rail (20) is fixedly connected with the fixing platform (16); two limit switches (19) are assembled on both ends of the fixing platform (16); the screw rod (22) is connected with both ends of the fixing platform (16); the sliding block (21) is connected with the screw rod (22) and the guide rail (20), wherein the sliding block connector (23) is fixedly connected with the sliding block (21) and a piston rod of the motion hydraulic cylinders (7a); the hydraulic cylinder connector (24) is fixedly connected with the motion hydraulic cylinders (7a) and fixing platform (16); a bottom end of each of the hydraulic sensors (25) is fixedly connected with the motion hydraulic cylinder (7a) and a top end of each of the hydraulic sensors (25) is fixedly connected with the platform hydraulic cylinder (7b) through one of the hydraulic pipes (26); the DC motor (17) is fixedly connected with the fixing platform (16) and the screw rod (22); the encoder (18) is fixedly connected with the DC motor (17); the fixing platform (16) is a U-shaped structure with two mounting holes which is for fixing the movement assemblies and components; wherein the DC motor (17) is a standard DC motor which is for driving the screw rod (22); the encoder (18) is a standard encoder which is for sampling velocity and acceleration information of the DC motor (17); the limit switches (19) are standard limit switches which are for checking a position of the sliding block; the guiding rail (20) is a standard guiding rail which guides the sliding block (21), wherein the sliding block (21) is a threaded cubic sliding block which is for transforming a rotary motion of the screw rod (22) into a translational motion; the screw rod (22) is a standard screw rod which is for connecting the DC motor (17) and the sliding block (21); the sliding block connector (23) is an L-shaped structure with two through holes, which is for connecting the sliding block (21) and the two motion hydraulic cylinders (7a); the hydraulic cylinder connector (24) is an L-shaped structure with two through holes, which is for connecting the fixing platform (16) and the two motion hydraulic cylinder (7a); the hydraulic sensors (25) are standard hydraulic sensors which are for checking a liquid pressure in the hydraulic pipes (26);

wherein twelve of the 24 hydraulic pipes (26) are connected with the movement assemblies and the operating handle parallel platform assembly and the rest twelve hydraulic pipes are connected with the movement assemblies and the fixing assembly parallel platform assembly which is connected with the top platform connecting plate (9) and the fixing assemblies, wherein each of the hydraulic pipes are standard hydraulic pipe for power transfer for the parallel platform assemblies and the movement assemblies.

* * * * *